United States Patent [19]

Suresh et al.

[11] Patent Number: 4,659,689

[45] Date of Patent: Apr. 21, 1987

[54] METHOD OF PREPARATION OF HIGH ACTIVE PHASE (AMM)OXIDATION CATALYSTS WITH IMPROVED PERFORMANCE AND ATTRITION RESISTANCE

[75] Inventors: Dev D. Suresh, Macedonia; Robert J. Zagata, Seven Hills; Maria S. Friedrich, Lyndhurst; Michael J. Seely, Chagrin Falls, all of Ohio

[73] Assignee: The Standard Oil Company, Cleveland, Ohio

[21] Appl. No.: 836,269

[22] Filed: Mar. 5, 1986

[51] Int. Cl.[4] .................. B01J 23/04; B01J 23/18; B01J 23/28

[52] U.S. Cl. .................. 502/311; 558/324

[58] Field of Search .................. 502/311, 243, 249

[56] References Cited

U.S. PATENT DOCUMENTS

| | | | |
|---|---|---|---|
| T864,008 | 12/1968 | Campbell | 252/411 |
| 3,625,867 | 12/1971 | Yoshino et al. | 252/456 |
| 4,070,390 | 1/1978 | Umemura et al. | 502/312 X |
| 4,192,776 | 3/1980 | Grasselli et al. | 502/311 X |
| 4,212,766 | 7/1980 | Brazdil et al. | 502/311 X |
| 4,228,098 | 10/1980 | Aoki et al. | 260/465.3 |
| 4,315,838 | 2/1982 | Miller et al. | 252/448 |
| 4,368,303 | 1/1983 | McDaniel | 525/106 |
| 4,425,255 | 1/1984 | Toyoda et al. | 502/38 |
| 4,425,260 | 1/1984 | Ebner | 502/255 |
| 4,495,109 | 1/1985 | Grasselli et al. | 260/465.3 |
| 4,508,848 | 4/1985 | Dolhyj et al. | 502/239 |

Primary Examiner—W. J. Shine
Attorney, Agent, or Firm—M. F. Esposito; J. E. Miller; L. W. Evans

[57] ABSTRACT

A process for the preparation of bismuth molybdate catalyst comprising (1) adding a dried mixture of metal salts of the active phase of the catalyst to an aqueous sol containing a support material for the active phase, (2) adding an acid to this slurry, (3) heating the slurry to dryness and (4) calcining the dried precursor to form the catalyst.

8 Claims, No Drawings

METHOD OF PREPARATION OF HIGH ACTIVE PHASE (AMM)OXIDATION CATALYSTS WITH IMPROVED PERFORMANCE AND ATTRITION RESISTANCE

BACKGROUND OF THE INVENTION

The present invention relates to a method of preparing a high active phase ammoxidation catalyst having improved performance and attrition resistance. In particular, the present invention is directed to a method of preparing a bismuth molybdate ammoxidation catalyst characterized by containing greater than 60% active phase and less than 40% support. The catalysts prepared by the method of the present invention exhibit improved attrition resistance while maintaining their catalytic activity to the ammoxidation of propylene or isobutylene with ammonia to produce acrylonitrile or methacrylonitrile.

Any commercial fluid bed ammoxidation catalyst comprises two essential parts. The first part is an active phase which usually is mixture of transition metal oxides promoted with alkali, alkaline earth and/or amphoteric metal oxides. This active phase is generally recognized as being responsible for the catalytic activity required for the conversion of hydrocarbons to useful products. The second part of the commercial catalyst is the inert support which is generally thought of as not participating in the catalytic reaction. The active phase of the catalyst is usually soft and becomes fine and powdery upon continued use in a reactor. The support material has oxygen atoms associated with it which are too tightly bonded to be removed under normal reactant conditions. Accordingly, the support is characterized as being hard and is added to increase the hardness (the attrition resistance) of the catalyst and make it suitable for operation in a commercial fluid bed reactor.

An appropriate blend of both the active phase and the support is crucial to obtain a suitable catalytic activity and hardness (attrition resistance) for the catalyst. Typically, the ratio of active phase to support in fluid bed catalysts is between about 50–60%:50–40%. Previously, any increase in the percent active phase increased the activity of the catalyst, but decreased the attendant attrition resistance. Conversely, any increase in the percent support increased the attrition resistance of the catalyst, but was accompanied by a decrease in the activity of the catalyst. For a clear teaching of the effects of too much active or support phase in a commercial catalyst, see U.S. Pat. No. 4,228,098 herein incorporated by reference. Accordingly, the desire to increase the percent of active material in the catalyst while maintaining its attrition resistance at a commercially acceptable level, while recognized, has until now remained elusive. The process of the present invention is directed to solving this long felt need and is particularly applicable to catalysts which have a high active phase (greater than 60% active phase) and a low support phase (less than 40% support). It is also envisioned that the method of the present invention is completely applicable to conventional commercial catalysts.

SUMMARY OF THE INVENTION

It is the primary object of the present invention to provide a novel method of preparing an ammoxidation catalyst having improved performance and attrition resistance.

It is another object of the present invention to provide a method of preparing an ammoxidation catalyst containing greater than 60% active phase and less than 40% support.

It is a further object of the present invention to provide a novel method of preparing fluid bed catalyst which improves the attrition resistance of the catalyst.

Additional objects, advantages and novel features of the invention will be set forth in part in the description which follows, and in part will become apparent to those skilled in the art upon examination of the following, or may be learned by practice of the invention. The objects and advantages of the invention may be realized and attained by means of the instrumentalities and combinations particularly pointed out in the appended claims.

To achieve the foregoing and other objects and in accordance with the purpose of the present invention as embodied and broadly described herein, the process of producing an ammoxidation catalyst according to the present invention comprises adding a dried mixture comprising the metal salts of the active phase of the catalyst to an aqueous sol containing an inert support material for the catalyst and an acid, heating the resulting aqueous slurry to dryness to obtain a dried catalyst precursor comprising a mixture of the active metal salts on the inert support material, and calcining the precursor to form the catalyst.

In a preferred embodiment of the present invention, the process further comprises contacting the catalyst with a reducing gas subsequent to calcining the precursor.

In accordance with another aspect of the present invention, as embodied and broadly described herein, the process of preparing the ammoxidation catalyst comprises preparing an aqueous solution comprising a mixture of the metal salts of the active phase of the catalyst, heating the aqueous solution to drive off the water and obtain a dried precipitate comprising a mixture of the metal salts, adding the dried precipitate to an aqueous sol containing an inert support for the catalyst and an acid to form a slurry, heating the slurry to dryness to obtain a catalyst precursor comprising a mixture of active metal salts on the inert support material, calcining the precipitate and reducing the calcined precipitate by contact with a reducing atmosphere to form the catalyst.

The process of the present invention is directed to a two-stage preparation method for preparing ammoxidation catalysts. In the frst stage of the method, a dried precipitate of the metal salts of the active phase of the catalyst is formed. In the second stage of the procedure, this dried precipitate is added to an aqueous sol containing an acid. It is the combination of the separate formation of the dried precipitate containing the active phase of the catalyst prior to the addition to the acidified aqueous sol which results in the remarkable improvements achieved by the process of the present invention. Applicants have found that catalysts prepared by this procedure exhibit remarkable attrition resistance when used in fluid bed ammoxidation procedures. In addition, the subsequent reduction of the catalyst by contact with a reducing gas results in a catalyst having high selectivity during ammoxidation as well as improved attrition resistance. The resulting procedure for the preparation of the ammoxidation catalyst provides a good commercial acrylonitrile catalyst having attrition resistance and selectivity well within the parameters desired for commercial catalysts.

Reference will now be made in detail to the present preferred embodiments of the invention.

DETAILED DESCRIPTION OF THE INVENTION

In general, the process of the present invention is directed to the preparation of bismuth-molybdenum catalyst systems used in the ammoxidation of propylene or isobutylene to acrylonitrile or methacrylonitrile. The process according to the present invention of preparing the bismuth-molybdate catalyst system comprises adding a dried mixture comprising the metal salts of the active phase of the catalyst to an aqueous sol containing the support material for the catalyst to form a slurry and adding an acid to the slurry. The slurry is then heated to evaporate the water and obtain a dried catalyst precursor comprising a mixture of the active metal salts on the inert support material. The resulting dried precipitate is calcined at a high temperature preferably between 500° C. to 800° C. to form the catalyst.

Preferably the process of the present invention is directed to producing catalyst containing greater than 60% active phase and less than 40% inert phase. Most preferably, the catalyst comprises over 70% active phase and less than 30% inactive phase.

In another preferred embodiment of the present invention, the catalyst is reduced by contacting the catalyst with a reducing gas at an elevated temperature subsequent to calcining. The reduction can be done by using hydrocarbons, hydrogen, ammonia or combinations thereof. The extent of the reduction is not critical. However, a deep reduction at a temperature (i.e. 460° C.) higher than the reaction temperature of ammoxidation is preferred.

The acid added to the aqueous catalyst slurry containing active phase and silica sol prior to ball milling is preferrably a mineral acid such as nitric or hydrochloric. However, organic acids such as acetic and oxalic may also be used. In the case of nitric acid, the concentration of the nitric acid in the sol is important. A range of between 25% to 40% nitric acid based upon the theoretical nitrates present in the catalyst before denitrification is preferred. Preferably, the addition of 33% nitric acid based upon the theoretical presence of the nitrates in the catalyst before denitrification is utilized in the practice of the present invention.

In a further preferred embodiment of the present invention, the dried mixture comprising the metal salts of the active phase of the catalyst is prepared by forming an aqueous solution comprising a mixture of the metal salts of the active phase of the catalyst, heating this aqueous solution to evaporate the water to obtain a dried precipitate comprising the mixture of the metal salts. Typically, the metal salts used in this procedure are salts soluble in water or nitric acid. Examples of the types of salts utilized in the procedure are nitrates, ammonium salts, chlorides, sulfates and salts of organic acids such as oxalic and acetic. However, it is clear that it is preferable to use the ammonium salt of molybdenum and in respect to the other sources of active metals to employ the nitrate salts.

In a still further preferred embodiment of the present invention, the dried precipitate comprising the mixture of the salts of the active metal phase of the catalyst is then added to the aqueous sol containing the inert support material, then the acid is added. This solution is heated to drive off the water to form a dried catalyst precursor comprising the mixture of the metal salts on an inert support.

Subsequently, the precursor is heated to a temperature sufficient to denitrify the metal salts, and calcined. Typically, the temperature utilized for denitrification is between 350° C. to 450° C. Denitrification is usually completed between about 1 to 4 hours, typically 3 hours being satisfactory.

Calcination of the dried slurry product typically takes place at a temperature of between 500°–800° C. Preferably, between 525°–575° C. for about 1 to 4 hours.

Usually the calcination is performed using an ordinary kiln such as a tunnel type or a rotary type.

In another preferred embodiment of the present invention, the slurry obtained by the addition of the dried metal precipitate and the silicon sol is spray dried using an ordinary spray drying apparatus to obtain the dried spherical particles. The spraying of the slurry may be conducted by any type of method usually employed in industry, e.g., a centrifugal type, a two-fluid nozzle type or a high pressure nozzle type spray method.

As stated previously, the present invention is directed in general to a novel process for the formation of bismuth-molybdate based catalyst useful in the ammoxidation of propylene to acrylonitrile. Typically, the bismuth-molybdate based catalysts are characterized by the following formula:

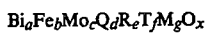

$$Bi_aFe_bMo_cQ_dR_eT_fM_gO_x$$

wherein

Q is at least one element selected from alkali metals, Tl, In, Cu, Ag;

R is at least one element selected from W, Cr, Ce, Zn, Ge, Mn, Pb, Ba, Te, Sn;

T is at least one element selected from phosphorus, arsenic, antimony, boron;

M is at least one element selected from cobalt, magnesium and nickel;

wherein a, b and c are numbers in the range of 0.1 to 12;

d is between 0.01 to 8;

e is between 0 to 8;

f is between 0 to 6;

g is between 0 to 12;

x is a number determined by the valency requirements of the other elements present.

In a further preferred embodiment of the present invention, the silica sol containing the acid may also contain a promoting element for the catalyst such as an alkali metal. Most preferably, the promoting element may comprise cesium, potassium, or sodium or mixtures of these elements.

The catalyst prepared by the process of the present invention can be used in the ammoxidation reaction of propylene for the preparation of acrylonitrile or the ammoxidation of isobutylene for the preparation of methacrylonitrile. The catalysts prepared by this procedure of the present invention exhibit a remarkably improved selectivity to these reactions as well as a remarkably improved attrition resistance. Catalysts prepared by the process of the present invention produce acrylonitrile having yields of over 75% with an attrition resistance of below 15%. Both of these figures are well within the accepted commercial parameter for acrylonitrile catalyst.

The present invention will now be illustrated in detail by the following examples, which should not be construed as limiting the scope of the present invention.

EXAMPLES AND COMPARATIVE EXAMPLE

The following examples were conducted using a catalyst having the following formula:

$$80\%K_{0.1}Ni_{2.5}Co_{4.5}Fe_2Cr_1Bi_1W_{0.5}Mo_{12}O_x - 20\%SiO_2$$

Obviously, this catalyst is characterized as containing a high active metal phase (80%) and low inert phase (20%) and would be expected to provide good selectivity to acrylonitrile product but poor attrition resistance. As the following examples illustrate. these catalyst prepared by conventional procedure have completely unacceptable attrition resistance while catalyst prepared by the procedure of the present invention have acceptable and significantly improved attrition resistance and selectivity.

EXAMPLE 1A

A catalyst comprising $80\%K_{0.1}Ni_{2.5}Co_{4.5}Fe_2Cr_1Bi_1W_{0.5}Mo_{12}O_x - 20\%SiO_2$ was prepared by conventional procedures (see for example, U.S. Pat. No. 4,228,098 herein incorporated by reference). The $SiO_2$-sol was mixed with an aqueous mixture of the salts of the active phase metals, spray dried, denitrified at 425° C. and calcined at 575° C. for 2 hours.

EXAMPLES 1-6

A catalyst comprising $80\%K_{0.1}Ni_{2.5}Co_{4.5}Fe_2Cr_1Bi_1W_{0.5}Mo_{12}O_x - 20\%SiO_2$ was prepared by a two-stage procedure. In Examples 1 and 2, an aqueous mixture of the salts of the active phase metals was prepared, spray dried and denitrified. The silica sol was mixed with the active phase and the mixture was ball-milled overnight. It was then spray dried again, denitrified at 425° C. for 3 hours and calcined at 575° C. for 2 hours.

In Examples 3 and 4, the active phase was not denitrified, but was mixed with the silica sol after spray drying. In Example 5, half of the active phase powder was spray dried and denitrified, while the other half was only spray dried, before being mixed with the silica sol. In Example 6, the catalyst slurry was spray dried at a higher than usual temperature after the silica sol was added. After silica sol addition, the catalysts of Examples 3-6 were processed as described for Examples 1 and 2.

EXAMPLE 7

The catalyst was prepared as described in Example 2, except that 72g of 70% $HNO_3$ per pound of active phase was added to the silica sol-active phase mixture before ball milling. The results set forth in Table I clearly demonstrate the remarkable improvement in attrition resistance for the catalyst.

EXAMPLE 8

The catalyst was prepared as described in Example 3, except that an aqueous slurry of the spray dried first stage powder was ball milled and the silica sol was added after ball milling. The results set forth in Table I show that attrition resistance rises to an unacceptable level.

EXAMPLE 9

Substantially the same procedure as set forth in Example 7. The results set forth in Table I again verify the improvement in attrition of the resulting catalyst. In addition, the calcined catalyst is subjected to a deep reduction by contact with ammonia at 460° C. for 1 hour. The reduction step clearly regenerates the catalyst to a state where the yield of acrylonitrile is 77.1% with a 78% selectivity.

EXAMPLES 10 and 11

The following examples are performed in substantially the same manner as described in Example 9. However, Example 10 was conducted with a catalyst slurry containing 50 g of 70% $HNO_3$ per pound of active phase powder and Example 11 with a catalyst slurry containing 90 g of 70% $HNO_3$ per pound of active phase powder. The results demonstrate that the amount of $HNO_3$ added to the catalyst slurry will affect the attrition resistance of the catalyst.

EXAMPLES 12-14

The procedure set forth in Example 7 was followed except that the silica sol contained $Mo_{0.03}$, $K_{0.02}$ or $Cs_{0.02}$, respectively. The results set forth in Table I show that promoters added to the silica sol do not affect attrition resistance of the catalyst. As in Example 7, the catalyst precursor slurry also contained nitric acid. Moreover, in Example 14, the Cs promoted catalyst was subjected to a deep reduction at 460° C. for 1 hour in ammonia. This catalyst exhibited 78% acrylonitrile yield and 79.9% selectivity.

EXAMPLE 15

The procedure set forth in Example 7 was followed except that the silica is provided in the form of dry particles (i.e. Aerosil). The results obtained are set forth in Table 1.

EXAMPLE 16

The procedure of Example 7 was followed except that HCl was substituted for $HNO_3$. The results set forth in Table I clearly show that other mineral acid such as HCl produce a catalyst having a commercially acceptable attrition resistance (i.e., below 15%).

TABLE I $80\% K_1Ni_{2.5}Co_{4.5}Fe_2Cr_1Bi_1W_{.5}Mo_{12}O_x - 20\% SiO_2$
TWO-STAGE 0/20 PREPARATIONS)

| EXAMPLE | FSO | $HNO_3$ | PROMOT | ATTRIT. RESISTANCE AFTER 20 HOURS | | | B.E.T. S.A. ($M^2/G$) | PORE VOL. (CC/G) | 1½" REACT | | PACKED FL. BD. MICROREACTOR | |
|---|---|---|---|---|---|---|---|---|---|---|---|---|
| | | | | 0-5 | 5-20 | TOTAL | | | % AN | % SEL | % AN | % SEL |
| | | | | | | | | | | | ("OLD" SIM. PRESS) | |
| 1A | 1-STAGE | — | — | 32.9 | 20.2 | 53.1 | 17.2 | 0.32 | 77.3 | 77.7 | | |

TABLE I-continued

80% K.1NI2.5CO4.5FE2CR1BI1W.5MO12Ox—20% SIO2
TWO-STAGE 0/20 PREPARATIONS)

| EXAMPLE | FSO | HNO3 | PROMOT | AIIRIT. RESISTANCE AFTER 20 HOURS | | | B.E.T. S.A. ($M^2/G$) | PORE VOL. (CC/G) | 1½" REACT | | PACKED FL. BD. MICROREACTOR | |
|---|---|---|---|---|---|---|---|---|---|---|---|---|
| | | | | 0-5 | 5-20 | TOTAL | | | % AN | % SEL | % AN | % SEL |
| 1 | PREP. 100% DN** (DENITRIFICATION) | — | — | 35.2 | 11.0 | 46.2 | 23.3 | 0.26 | | | | |
| 2 | 100% DN | — | — | 30.9 | 11.6 | 42.5 | 21.9 | 0.28 | | | | |
| 3 | 100% SD (SPRAY DRIED) | — | — | 17.3 | 8.0 | 25.3 | 21.0 | 0.33 | 73.9 | 75.4 | 81.5 | 82.1 |
| 4 | 100% SD* | — | — | 33.4 | 14.7 | 48.1 | 19.5 | 0.31 | | | | |
| 5 | 50 DN/50 SD | — | — | 34.8 | 14.6 | 49.4 | 21.3 | 0.31 | | | | |
| 6 | 100 SD/HI TEMP | — | — | 31.2 | 12.2 | 43.4 | 20.4 | 0.32 | | | | |
| 7 | 100% DN | YES | — | 2.7 | 8.4 | 11.1 | 22.1 | 0.20 | | | 78.7 | 82.1 |
| 8 | 100% SD (SIO2 LATER) | — | — | 12.7 | 8.3 | 21.0 | 20.8 | 0.34 | | | | |
| | | | | | | | | | | | (SIM. 14 PSIG) | |
| 9 | 100% DN | YES | — | 2.9 | 5.9 | 8.8 | 18.7 | 0.21 | 66.8 | 75.6 | 66.9 (77.1 | 75.1 78.0 R/R) |
| 10 | " | LESS | — | 6.2 | 14.4 | 20.6 | 17.5 | 0.23 | | | | |
| 11 | " | MORE | — | 6.1 | 17.9 | 24.0 | 18.0 | 0.24 | | | | |
| 12 | " | YES | MO0.3 | 2.3 | 6.9 | 9.2 | 14.2 | 0.21 | 64.9 | 77.4 | | |
| 13 | " | YES | K.02 | 1.9 | 6.0 | 7.9 | 16.9 | 0.21 | 55.7 | 73.4 | | |
| 14 | " | YES | CS.02 | 4.2 | 7.8 | 12.0 | 13.5 | 0.21 | 62.2 | 74.3 | 63.0 (78.0 | 73.8 79.9 R/R) |
| 15 | AEROSIL (15 SOL/5 FUMED) | YES | — | 5.2 | 13.6 | 18.8 | 20.5 | 0.25 | 69.1 | 76.7 | | |
| 16 | 100% DN | HCL | — | 3.0 | 9.8 | 12.8 | 14.3 | 0.22 | | | | |

*NO BALL-MILLING,
**4-HR. BALL-MILLING

The foregoing description of the preferred embodiments of the invention has been presented for purposes of illustration and description. It is not intended to be exhaustive or to limit the invention to the precise form disclosed, and obviously many modifications and variations are possible in light of the above disclosure. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A process for producing a supported bismuth molybate catalyst comprising (1) adding a dried mixture comprising the metal salts of the active phase of said catalyst to an aqueous sol containing a support material for the catalyst and an acid to form a slurry, (2) heating the resulting aqueous slurry to dryness to form a dried catalyst precursor and (3) calcining the dried mixture to form the catalyst.

2. The process of claim 1 further comprising (4) contacting the catalyst with a reducing gas subsequent to calcining the precursor.

3. The process of claim 1 wherein the ratio of active phase to support for said catalyst is greater than 60:less than 40.

4. The process of claim 3 wherein said ratio is 80:20.

5. The process of claim 1 further comprising preparing said dried mixture by adding said metal salts of the active phase of the catalyst to water to form a solution, heating the aqueous solution to drive off the water and obtain a dried precipitate comprising a mixture of the metal salts.

6. The process of claim 5 wherein said metal salts of said active phase are nitrates.

7. The process of claim 6 further comprising heating said dried catalyst precursor between 350° C. to 450° C. to denitrify said precursor prior to calcination.

8. The process of claim 7 wherein said aqueous sol contains an alkali metal.

* * * * *